United States Patent
Bru Roig et al.

(10) Patent No.: US 10,196,332 B2
(45) Date of Patent: Feb. 5, 2019

(54) PROCESS FOR PREPARING 3-METHYLCYCLOPENTADECANE-1,5-DIOL

(71) Applicant: BASF SE, Ludwigshafen am Rhein (DE)

(72) Inventors: Miriam Bru Roig, Heidelberg (DE); Stefan Rüdenauer, Weinheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/761,699

(22) PCT Filed: Sep. 20, 2016

(86) PCT No.: PCT/EP2016/072215
§ 371 (c)(1),
(2) Date: Mar. 20, 2018

(87) PCT Pub. No.: WO2017/050713
PCT Pub. Date: Mar. 30, 2017

(65) Prior Publication Data
US 2018/0346397 A1 Dec. 6, 2018

(30) Foreign Application Priority Data
Sep. 22, 2015 (EP) .................................. 15186290

(51) Int. Cl.
*C07C 29/132* (2006.01)
*C07C 45/57* (2006.01)

(52) U.S. Cl.
CPC ............. *C07C 29/132* (2013.01); *C07C 45/57* (2013.01); *C07C 2601/18* (2017.05); *C07C 2602/32* (2017.05)

(58) Field of Classification Search
CPC ......... C07C 45/66; C07C 45/64; C07C 41/02; C07C 49/487; C07C 49/587; C07C 45/28; C07C 29/132; C07C 45/57; C07C 2602/32; C07C 2601/18; B01J 2531/847; B01J 2531/64
See application file for complete search history.

(56) References Cited

U.S. PATENT DOCUMENTS 4,335,262 A 6/1982 Schulte-Elte et al.
2017/0362153 A1* 12/2017 Tanino .................... C07B 61/00

FOREIGN PATENT DOCUMENTS

| CH | 519454 A | 2/1972 |
| GB | 1205047 A | 9/1970 |
| GB | 1205049 A | 9/1970 |

OTHER PUBLICATIONS

U.S. Appl. No. 15/575,169, Rüdenauer et al.
U.S. Appl. No. 15/578,959, Bru Roig et al.
International Search Report for PCT/EP2016/072215 dated Nov. 25, 2016.
Written Opinion of the International Searching Authority for PCT/EP2016/072215 dated Nov. 25, 2016.

* cited by examiner

*Primary Examiner* — Jafar F Parsa
(74) *Attorney, Agent, or Firm* — Drinker Biddle & Reath LLP

(57) ABSTRACT

The present invention relates to a process for preparing 3-methylcyclopentadecane-1,5-diol (I) by hydrogenolysis of 14-methyl-16,17,18-trioxatricyclo[10.3.2.1]octadecane (II). The invention further relates to a process for preparing 3-methylcyclopentadecane-1,5-diol is a macrocyclic diol that can serve as precursor for a macrocyclic odorant, such as muscone and muscenone.

19 Claims, No Drawings

PROCESS FOR PREPARING 3-METHYLCYCLOPENTADECANE-1,5-DIOL

CROSS-REFERENCE TO RELATED APPLICATIONS

This application is a national stage application (under 35 U.S.C. § 371) of PCT/EP2016/072215, filed Sep. 20, 2016, which claims benefit of European Application No. 15186290.1, filed Sep. 22, 2015, both of which are incorporated herein by reference in their entirety.

The present invention relates to a process for preparing 3-methylcyclopentadecane-1,5-diol (I) by hydrogenolysis of 14-methyl-16,17,18-trioxatricyclo[10.3.2.1]octadecane (II).

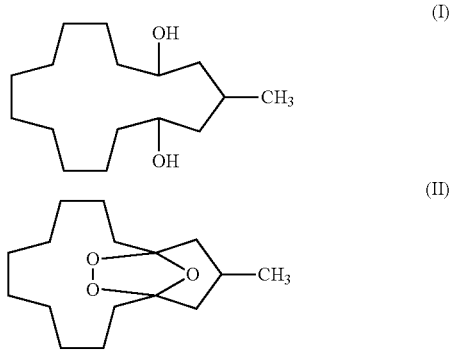

3-methylcyclopentadecane-1,5-diol is a macrocyclic diol that can serve as precursor for macrocyclic musk odorants, such as muscone (3-methylcyclopentadecanone) and muscenone (dehydromuscone, 3-methylcyclopentadecenone) (U.S. Pat. No. 4,335,262).

CH 519 454 and GB 1 205 049 describe the ozonization of unsubstituted and 3-methyl substituted bicyclo[10.3.0]pentadecene[1(12)] and subsequent reductive cleavage of the ozonization product, e.g. 14-methyl-16,17,18-trioxatricyclo[10.3.2.1]octadecane compound (II), by sodium sulfite, triphenylphosphine or hydrogenolysis in the presence of a Pd/C catalyst yielding the corresponding cyclopentadecane-1,5-dione.

Typically, in the presence of conventional Raney nickel catalysts, the hydrogenation of an ozonide under moderate conditions (such as less than 120° C. and less than 15 MPa hydrogen pressure) and within an acceptable reaction time basically only yields the corresponding diketone. The conversion of an ozonide to the corresponding diol requires much more drastic conditions, such as a temperature of at least 140° C. and a hydrogen pressure of at least 18 MPa. Such conditions are difficult to handle and require expensive high pressure equipment and safety measures, in particular on the production scale.

It was surprisingly found that the use of molybdenum-doped Raney nickel as a catalyst allows for an easier and more effective conversion of an ozonization product of formula (II) to a diol of formula (I), even at moderate conditions of not more than 5 MPa hydrogen pressure. The temperature required will generally not exceed 120° C. At these conditions complete conversion of the 14-methyl-16,17,18-trioxatricyclo[10.3.2.1]octadecane (II) with high selectivity can be achieved within less than 36 h.

Accordingly, the present invention relates to a process for preparing 3-methylcyclopentadecane-1,5-diol of formula (I). The process comprises the hydrogenolysis of an ozonide of formula (II) in the presence of a base and a catalyst comprising molybdenum-doped Raney nickel.

It is a particular advantage of the invention that by using a molybdenum-doped Raney nickel, the hydrogenolysis of the ozonide (II) to the desired diol compound (I) can be achieved under moderate conditions. Said moderate conditions are characterized by a hydrogen pressure of 5 MPa or less, in particular from 1 to 5 MPa, preferably from 1.5 to 4 MPa and more preferably from 1.7 to 2.5 MPa. The temperature required will generally not exceed 120° C., in particular not exceed 110° C., and will frequently be in the range of from 50 to 120° C., in particular from 55 to 110° C., more particularly from 60° C. to 100° C., preferably from 65° C. to 80° C. and more preferably from 68° C. to 75° C.

In order to achieve complete conversion of the compound of formula (II), the reaction time under said moderate conditions will generally not exceed 36 h, in particular not exceed 25 h and preferably not exceed 20 h. Frequently, the moderate conditions will be applied for a duration of up to 36 h, in particular up to 25 h or up to 20 h, in order to achieve complete conversion. Longer reaction times will generally not be required but it is of course possible to apply longer reaction times. Usually, the reaction time under said moderate conditions is from 2 to 36 h, in particular from 3 to 36 h or from 5 to 36 h or from 8 to 36 h or from 5 to 25 h or from 5 to 20 h or from 8 to 25 h or from 8 to 20 h.

The ozonide of formula (II) can be prepared by ozonization of the bicyclic olefine compound of formula (III)

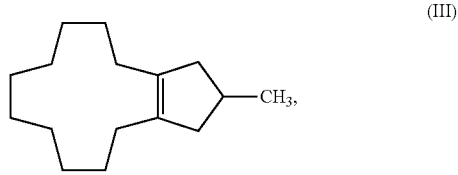 [SMILES: CC1CC2=C(CCCCCCCCCC2)C1]

for example as described in GB 1 205 049. Said ozonization can be carried out in a liquid phase comprising the compound of the formula (III) and an organic solvent or solvent mixture. Suitable organic solvents include, but are not limited to alkanols, in particular $C_1$-$C_4$-alkanols, such as methanol, and organic solvent mixtures consisting essentially, e.g. to at least 80 wt-%, 90 wt-%, 95 wt-% or entirely, of at least one alkanol, in particular a $C_1$-$C_4$-alkanol, such as methanol, and at least one halogenated, e.g. chlorinated hydrocarbon, such as dichloromethane. The ozone is usually introduced as an ozone-oxygen mixture with cooling, e.g. to −10° C. or lower, over several hours, e.g. for about 1 to 10 h, in particular for 4 to 8 h. After the addition of ozone is complete, the ozonization reaction mixture may be incubated for an additional period, e.g. from 1 to 36 h, in particular from 4 to 24 h. Frequently, 10 to 50 mg ozone per g of the compound of formula (III) are used. For example, ozonization of (III) may be achieved by introducing 10-50 mg ozone per g compound of formula (III) per hour for about 4-8 h into the liquid phase at a temperature of at most −10° C. and incubationg the ozonization reaction mixture an additional period, e.g. from 1 to 36 h, in particular from 4 to 24 h (e.g. overnight) at the same temperature (e.g. −10° C. or lower).

The compound of formula (III) can be prepared from cyclododecanone according to the scheme below and methods as described, e.g., in CH 519 454.

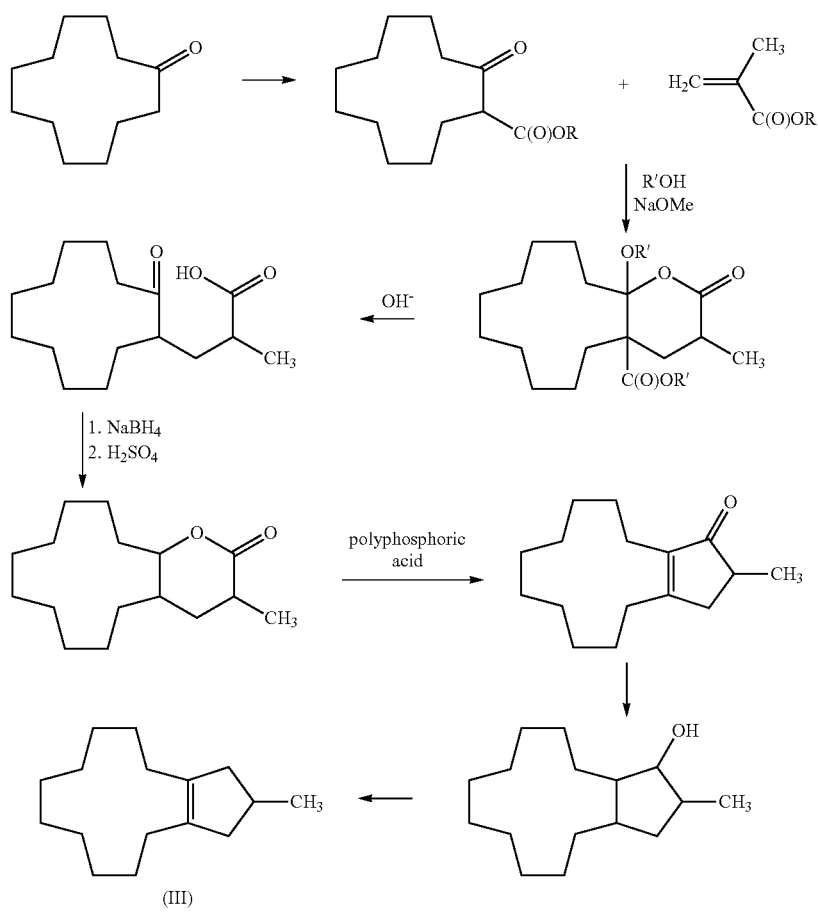

(III)

R and R' are independently selected from lower alkyl (e.g. methyl or ethyl)

In a particular embodiment of the invention, the ozonide of formula (II), which is used in the hydrogenolysis, is preferably purified to at least 75% purity, e.g. at least 80%, up to 90% or up to virtually 100% purity, prior to its use in the process of the present invention. For example, the ozonide of formula (II) can be isolated as a crystalline substance from a crude product solution obtained after ozonization of the compound of formula (III). The identity of the ozonide of formula (II) can be verified using methods such as $^1$H nuclear magnetic resonance ($^1$H-NMR) analysis and liquid chromatography (LC) or mass spectrometry (MS). However, the ozonide of formula (II) may also be used in impure form (e.g. less than 60%, about 50%, down to 40% purity) or as the solution obtained from the ozonization of the compound of formula (III) without further work-up.

In the process of the present invention, hydrogenolysis of the ozonide of formula (II) can be carried out in the absence of a liquid organic solvent or diluent. Alternatively, the ozonide of formula (II) can be dispersed or dissolved in a liquid organic solvent. Thus, hydrolysis can be carried out in a liquid phase comprising, or basically consisting of, the ozonide of formula (II), a liquid organic solvent, the base and, optionally, water, in particular where the based is provided as an aqueous solution. Suitable organic solvents are those, which are liquid at 23° C. and ambient pressure and include, but are not limited to, $C_1$-$C_4$-alkanols such as methanol, ethanol, isopropanol and mixtures thereof as well as mixtures with solvents that are inert under the reaction conditions such as aliphatic hydrocarbon solvents and aliphatic ethers. The concentration of the ozonide (II) may generally be in the range of from 2 to 200 g/l, in particular from 10 to 50 g/l or from 15 to 30 g/l, and preferably in the range of from 23 to 28 g/l.

The catalyst used in the process of the present invention comprises molybdenum-doped Raney nickel. Said molybdenum-doped Raney nickel usually contains (i) nickel (Ni) as the main component at amounts which are typically in the range of from 75 to 95 wt-%, in particular from 80 to 90 wt-% or from 84 to 88 wt-%, (ii) molybdenum (Mo) in amounts which are typically in the range of from 0.5 to 2.0 wt-%, in particular from 0.8 to 1.3 wt-% or from 0.9 to 1.1 wt-%, and (iii) one or more other metals. Said other metals may include, for example, aluminum (Al) and iron (Fe). Typically, the amount of aluminum, if present, is in the range of from 2.0 to 15.0 wt-%, in particular from 3.0 to 10.0 wt-% or from 4.0 to 6.0 wt-%. Typically, the amount of iron, if present, is in the range of from 0.00 to 0.30, e.g. from 0.05 to 0.20 or from 0.10 to 0.15 wt-%. The amounts of metals contained in the molybdenum-doped Raney nickel and indicated in wt-% herein are based on the total (dry) mass of the molybdenum-doped Raney nickel.

Molybdenum-doped Raney nickel is usually prepared from a composition that consists essentially of an alloy of nickel, molybdenum, aluminum and, optionally, iron. The impurities are those typical in the material (in nature and in proportion). The alloy is activated by treatment with an alkaline solution, e.g. a concentrated solution of NaOH, which leaches part of the Al and Mo out of the alloy.

In the process of the present invention, the molybdenum-doped Raney nickel can be used in pure form, i.e. the catalyst basically consists of the molybdenum-doped Raney nickel, or in combination with other materials such as inert support materials. Suitable inert support materials include, but are not limited to, inorganic oxides, e.g. alumina, silica, silica-alumina, magnesia, zinc oxide, titanium dioxide, zirconium dioxide, other inorganic materials, e.g. ceramics, metals, glass, activated carbon, silicon carbide, calcium carbonate and barium sulfate, and mixtures thereof.

The catalyst can be provided in various forms. For example, the catalyst can basically consist of molybdenum-doped Raney nickel in a monolithic form, e.g. honeycomb, or in the form of a divided product, e.g. pulverulent products (powder), solid or hollow beads, pellets, spheres, granules, extrudates, agglomerates, or other shaped bodies having e.g. a circular, oval, trilobite, quadrilobate or other cross-section. Alternatively, the catalyst can basically consist of a support material coated with a layer of molybdenum-doped Raney nickel, wherein the support material has a monolithic form, e.g. honeycomb, or the form of a divided product, e.g. solid or hollow beads, pellets, spheres, granules, extrudates, agglomerates, or other shaped bodies having a circular, oval, trilobite, quadrilobate or other cross-section.

The use of pure molybdenum-doped Raney nickel, i.e. molybdenum-doped Raney nickel without support material in the form of a divided product, in particular in the form of a powder is preferred. The mass-averaged particle size d(0.5) of such a powder is typically in the range of from 10 µm to 60 µm, in particular from 20 µm to 40 µm or from 24 µm to 32 µm, e.g. of about 28 µm Where the molybdenum-doped Raney nickel is in the form of a powder it is usually provided as a slurry in water, for safety reasons.

The form of the catalyst determines the measures required for separation of the catalyst from the reaction medium after hydrogenolysis in a known manner. Monolithic catalyst forms may remain in the reaction vessel while the reaction medium is withdrawn. Catalyst powders may have to be removed from the reaction medium by liquid-solid separation, such as filtration or centrifugation, while larger divided forms of catalyst, e.g. catalyst pellets or beads, can be separated from the reaction medium by simple deposition at the bottom of the vessel.

In the process of the present invention, molybdenum-doped Raney nickel is frequently used in amounts of at least 8 wt-%, in particular at least 10 wt-%, at least 15 wt-%, at least 18 wt-% or about 19 wt-%, e.g. 19±5 wt-%, relative to the mass of the ozonide of formula (II). The upper amount is less critical. Amounts corresponding to more than 30 wt-% molybdenum-doped Raney nickel relative to the mass of the ozonide of formula (II) typically do not provide additional benefits and are therefore not applied due to economic considerations.

Suitable bases for use in the process of the present invention include, but are not limited to, alkali metal hydroxides such as NaOH or KOH, with NaOH being particularly preferred. The base can be used as an aqueous solution. Typically, the concentration of the base in the hydrogenolysis reaction mixture (comprising the ozonide of formula (II), the base, the catalyst and, optionally, a liquid organic solvent or diluent) is in the range of from 5 mM to 50 mM, in particular from 8 mM to 40 mM or from 9 mM to 25 mM.

Generally, the hydrogenolysis reaction of the process of the present invention can be performed in accordance with standard procedures of organic chemistry. Expediently, the reaction is performed in a pressure vessel that allows temperature control of the reaction mixture such as, for example an autoclave, autoclave reactor, fixed-bed reactor or bubble-flow reactor.

The process of the invention can be designed such that the hydrogenolysis of the ozonide takes place either continuously or batchwise. Batchwise hydrogenolysis can be carried out in a reaction apparatus conventionally used for this purpose, e.g. an autoclave or stirred autoclave reactor, which is optionally equipped with metering devices. Continuous hydrogenolysis can be carried out, e.g., in a fixed-bed or bubble-flow reactor.

The reaction mixture can be subjected to conventional work-up including, for example, removal of the catalyst (e.g. by filtration), extractive work-up using organic solvents such as ethyl acetate, removal of volatiles and the like. The obtained crude product may be subjected to conventional purification measures including distillation or chromatography or combinations of such measures. Suitable distillation devices for the purification of the diols of formula (I) include, for example, distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof.

The process of the present invention can be utilized in the synthesis of macrocyclic compounds, in particular macrocyclic odorants such as muscone or muscenone.

Accordingly, the present invention further provides a process for preparing a macrocyclic odorant comprising the steps of:
(i) preparing a diol of formula (I) by the process described herein;
(ii) dehydrogenating and dehydrating the diol of formula (I) so as to form an enol-ether of formula (IV)

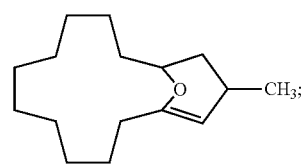

and
(iii) treating the enol-ether of formula (IV) with an acidic agent so as to form a compound of formula (V) (3-methylcyclopentadec-5-en-1-one)

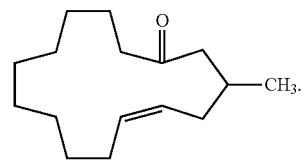

Optionally, the compound of formula (V) can be hydrogenated so as to form a compound of formula (VI) (3-methylcyclopentadecanone)

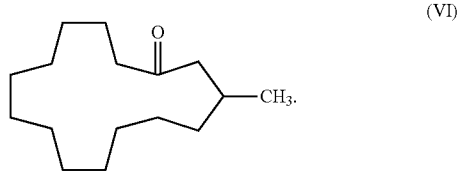 [SMILES: CC1CCCCCCCCCCCCC(=O)C1]
(VI)

Methods for converting a diol of formula (I) to an enol-ether of formula (IV) and further to a compound of formula (V) or (VI) are known in the art, e.g. from U.S. Pat. No. 4,335,262.

The conversion of a diol of formula (I) to an enol-ether of formula (IV) by dehydrogenation and dehydration can be effected in the presence of Raney copper (acting as a catalyst) at a temperature in the range of from 150° C. to 200° C. For example, Raney copper can be used in an amount corresponding to a mass ratio of Raney copper to diol of formula (I) in the range of from 1:1 to 1:20, in particular from 1:5 to 1:15 or from 1:6 to 1:10 (e.g. about 1:8). Part of the diol of formula (I) (e.g. a third to a fifth or about a forth) can be heated together with the Raney copper until a temperature in the range of from 150 to 200° C. (e.g. about 165° C.) is reached and then the remaining diol of formula (I) can be added slowly while maintaining the temperature. The enol-ether of formula (IV) can be directly collected from the reaction medium by distillation and can be purified by known methods such as vapor phase chromatography. For the preparation of the compound of formula (V), the enol-ether of formula (IV) can used in a purified form or as crude product.

The conversion of the enol-ether of formula (IV) to the compound of formula (V) can be effected by treatment of the enol-ether of formula (IV) with an acidic agent. Said conversion is usually carried out in an inert organic solvent. Suitable inert organic solvents include, but are not limited to, aromatic hydrocarbon solvents such as benzene, toluene, xylene and mixtures thereof, with toluene being preferred. Suitable acidic agents include, but are not limited to, protonic mineral acids, acidic cationic resins and diatomaceous earths, with phosphoric acid being preferred. For example, the conversion is carried out in a mixture of 80 wt-% aqueous phosphoric acid and an aromatic hydrocarbon solvent, expediently in a vessel equipped with a lateral distillation column which allows water to be taken off azeotropically. The mass ratio of phosphoric acid and compound of formula (IV) can, for example, be in the range of from 1:1 to 1:50, e.g. from 1:4 to 1:16 or from 1:6 to 1:10. The reaction temperature can be chosen within a wide range. A reaction temperature at the boiling point of the organic solvent is advantageous for practical reasons. After the conversion, the reaction medium is expediently neutralized with a base (e.g. aqueous sodium carbonate) and the produced compound of formula (V) can be isolated by extraction of the reaction medium with an organic solvent (e.g. toluene) and applying usual measures of working up organic extracts.

The compound of formula (V) can be converted into a compound of formula (VI) by hydrogenation of the compound of formula (V) in the presence of a catalyst. Suitable catalysts include noble metal catalysts such as platinum and palladium, e.g. 10 wt-% palladium on charcoal. The mass ratio of catalyst, e.g. 10 wt-% palladium on charcoal, to compound of formula (V) can, for example, be in the range of from 1:1 to 1:400, e.g. from 1:2 to 1:200 or from 1:3 to 1:150. The hydrogenation of the compound of formula (V) is expediently carried out in a pressure vessel that allows for controlling the temperature of the reaction mixture such as, for example, an autoclave, autoclave reactor, fixed-bed reactor or bubble-flow reactor. The hydrogenation can be carried out in the presence of an organic solvent, e.g. xylene or petrol ether. Suitable hydrogenation temperatures are, for example, in the range of from 60° C. to 110° C., e.g. from 80° C. to 100° C. For the hydrogenation, hydrogen pressures in the range of from 1-5 MPa, in particular 2-4 MPa can be used. The produced compound of formula (VI) can be purified by known methods such as vapor phase chromatography.

Definitions

The unit "wt-%" as used herein designates mass percentage.

Unless indicated otherwise, singular articles such as "a" or "an" used herein refer to both plural and singular of the subsequent noun.

EXAMPLES

I) Gas Chromatographic Analysis

Gas chromatography (GC) system and separation method:
GC-system: Agilent 7890 Series A;
GC-Column: DB-WAX (30 m (Length), 0.32 mm (ID), 0.25 µm (Film));
Injector at 230° C., detector at 280° C. and flow 1.5 ml.
Temperature program: 80° C. to 250° C. in 3° C./min, 250° C. for 15 min.

The yields of the exemplary syntheses described below which are expressed in wt-% were determined by GC.

II) Comparative Example 1

2 g 14-Methyl-16,17,18-trioxatricyclo [10.3.2.1]octadecane (80-90% purity determined by NMR) were dispersed at 25° C. in 100 ml methanol. To this mixture, 0.5 ml 10 wt-% NaOH in water and 0.5 g Raney Nickel (2400 Raney Nickel, CAS 7440-02-0) were added. In a 300 ml autoclave, the mixture was heated to a temperature of 70° C. and at this temperature the system was pressurized with 2 MPa hydrogen. The system was allowed to react under these conditions for 18 h. After this time, the autoclave was cooled down to room temperature and the Raney nickel was removed by filtration. The solvent was evaporated and the product was extracted with ethyl acetate so as to obtain 1.6 g of a crude product which contained 43 wt-% 3-methylcyclopentadecane-1,5-dione representing a yield of 45% based on the initial amount of 14-methyl-16,17,18-trioxatricyclo [10.3.2.1]octadecane. Only traces of 3-methylcyclopentadecane-1,5-diol were detected (<10 wt-% as determined by GC).

The Raney Nickel used as a catalyst in example 1 (2400 Raney Nickel) is a powder having a mass-averaged particle size d(0.5) in the range of 25-55 µm that is provided as a slurry in water with a mass ratio of dry catalyst and water of 50:50. In example 1, 2400 Raney Nickel was used in the form of the slurry precipitate (mass ratio of dry catalyst and water of 75:25). Analysis of the composition of 2400 Raney Nickel resulted in the detection of 75 wt-% Ni and 2.2 wt-% Fe, and 2.1 wt-% chromium (Cr) relative to the total (dry) mass of 2400 Raney Nickel. For said analysis a sample of 2400 Raney Nickel was dried overnight at 105° C. under argon. In addition of Ni, Fe and Cr, 2400 Raney Nickel contains aluminum.

III) Example 2

2 g 14-Methyl-16,17,18-trioxatricyclo [10.3.2.1]octadecane (80-90% purity determined by NMR) were dispersed at 25° C. in 100 ml of methanol. To this mixture, 0.5 ml 10 wt-% NaOH in water and 0.5 g molybdenum-doped Raney Nickel were added. In a 300 ml autoclave, the mixture was heated to a temperature of 70° C. and at this temperature the system was pressurized with 2 MPa hydrogen. The system was allowed to react under these conditions for 18 h. After this time, the autoclave was cooled down to room temperature and the Raney nickel was removed by filtration. The solvent was evaporated and the product was extracted with ethyl acetate so as to obtain 1.75 g of a crude product which contained 71 wt-% 3-methylcyclopentadecane-1,5-diol representing a yield of 80% based on the initial amount of 14-methyl-16,17,18-trioxatricyclo [10.3.2.1]octadecane.

The molybdenum-doped Raney Nickel used as a catalyst in the example 2 is a powder having a mass-averaged particle size d(0.5) of 33 μm (d(0.1): 8 μm; d(0.9): 101 μm) that is provided as a slurry in water with a mass ratio of dry catalyst and water of 50:50. In example 2, the molybdenum-doped Raney Nickel was used in the form of the slurry precipitate (mass ratio of dry catalyst and water of 75:25). Analysis of the catalyst composition resulted in the detection of 80 wt-% Ni and 1.0 wt-% Mo relative to the total (dry) mass of the molybdenum-doped Raney Nickel. The contents of C, H and N were each <0.5 wt-% and the content of S was <0.01 wt-%. Said analysis was not performed under an inert atmosphere and does not take any NiO, which might have formed, into account. In addition of Ni and Mo, the catalyst contains aluminum.

The invention claimed is:

1. A process for preparing a diol of formula (I)

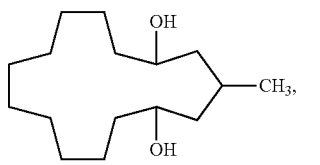

(I)

which comprises hydrogenolysis of an ozonide of formula (II)

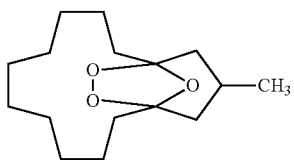

(II)

in the presence of a base and a catalyst comprising molybdenum-doped Raney nickel.

2. The process of claim 1, wherein hydrogenolysis is carried out at a hydrogen pressure of 5 MPa or less and at a temperature of 120° C. or less.

3. The process of claim 1, wherein the molybdenum-doped Raney nickel is used in an amount of at least 8 wt-% relative to the mass of the ozonide of formula (II).

4. The process of claim 1, wherein hydrogenolysis is performed in the absence of a liquid organic solvent or diluent.

5. The process of claim 1, wherein hydrogenolysis is carried out with the ozonide of formula (II) being dispersed in a liquid phase comprising the base, an organic solvent selected from $C_1$-$C_4$-alkanols, and optionally water.

6. The process of claim 5, wherein the ozonide of formula (II) is used in an amount of from 2 to 200 g/l relative to the solvent.

7. The process of claim 1, wherein the base is selected from alkali metal hydroxides.

8. The process of claim 1, wherein the concentration of the base is in the range of from 5 mM to 50 mM.

9. The process of claim 1, wherein hydrogenolysis is carried out at temperatures in the range of from 50° C. to 120° C., and at hydrogen pressures of from 1 to 5 MPa.

10. The process of claim 1, wherein the conditions for hydrogenolysis are applied over a period of for up to 36 h.

11. The process of claim 1, wherein hydrogenolysis is carried out continuously or batchwise.

12. The process of claim 1, further comprising the preparation of the ozonide of formula (II) by ozonization of a compound of formula (III)

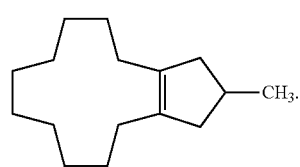

(III)

13. The process of claim 1, wherein the molybdenum-doped Raney nickel contains aluminum and from 75 to 95 wt-% nickel and from 0.5 to 2.0 wt-% molybdenum based on the total mass of the molybdenum-doped Raney nickel.

14. A process for preparing a macrocyclic odorant of the formulae (V) or (VI) comprising the steps of:
  (i) preparing a diol of formula (I)

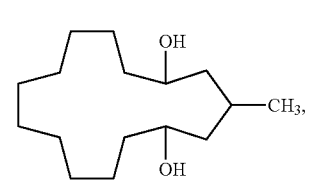

(I)

by carrying out the process of claim 1;
  (ii) dehydrogenating and dehydrating the diol of formula (I) so as to form an enol-ether of formula (IV)

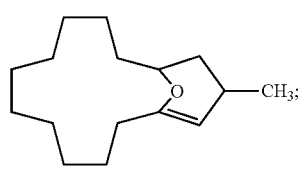

(IV)

and
  (iii) treating the enol-ether of formula (IV) with an acidic agent so as to form a compound of formula (V)

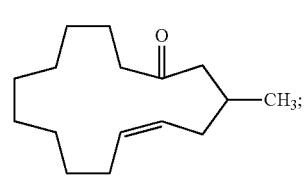

(V)

and optionally the step of
  (iv) hydrogenating the compound of formula (V) so as to form a compound of formula (VI)

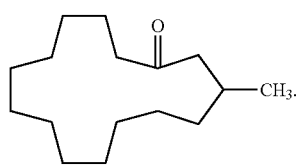 (VI)

15. The process of claim 1, wherein hydrogenolysis is carried out with the ozonide of formula (II) being dispersed in a liquid phase comprising the base, an organic solvent selected from the group consisting of methanol, ethanol or isopropanol, and mixtures thereof, and optionally water.

16. The process of claim 5, wherein the ozonide of formula (II) is used in an amount of from 10 to 50 g/l relative to the solvent.

17. The process of claim 1, wherein the base is selected from the group consisting of NaOH and KOH.

18. The process of claim 1, wherein hydrogenolysis is carried out at temperatures in the range of from 55° C. to 110° C., and at hydrogen pressures of from 1.5 to 4 MPa.

19. The process of claim 1, wherein the conditions for hydrogenolysis are applied over a period of 2 to 36 h.

* * * * *